(12) United States Patent
Long et al.

(10) Patent No.: US 6,875,222 B2
(45) Date of Patent: Apr. 5, 2005

(54) BLADE FOR RESECTION OF BONE FOR PROSTHESIS IMPLANTATION, BLADE STOP AND METHOD

(75) Inventors: Jack F. Long, Warsaw, IN (US); Brian John Maroney, Fort Wayne, IN (US); Roy Sanders, Tampa, FL (US); Kevin M. Cordes, Placerville, CA (US); Michael G. Fisher, El Dorado Hills, CA (US)

(73) Assignee: Depuy Products, Inc., Warsaw, IN (US)

( * ) Notice: Subject to any disclaimer, the term of this patent is extended or adjusted under 35 U.S.C. 154(b) by 65 days.

(21) Appl. No.: 10/235,219

(22) Filed: Sep. 5, 2002

(65) Prior Publication Data

US 2003/0176867 A1 Sep. 18, 2003

Related U.S. Application Data

(60) Provisional application No. 60/363,528, filed on Mar. 12, 2002.

(51) Int. Cl.$^7$ .......................... A61B 17/32; A61B 17/58; B23D 47/02
(52) U.S. Cl. .......................... 606/172; 606/102; 606/82; 606/178; 30/374
(58) Field of Search .............................. 606/74, 82, 96, 606/102, 172, 178; 30/370, 374, 375, 377, 505

(56) References Cited

U.S. PATENT DOCUMENTS

| | | | |
|---|---|---|---|
| 2,133,859 A | * 10/1938 | Hawley | 606/69 |
| 4,617,930 A | * 10/1986 | Saunders | 606/82 |
| 4,833,781 A | * 5/1989 | Allen | 30/377 |
| 5,092,869 A | 3/1992 | Waldron | |
| 5,263,972 A | * 11/1993 | Evans et al. | 606/176 |
| 5,326,365 A | 7/1994 | Alvine | |
| 5,520,692 A | 5/1996 | Ferrante | |
| 5,571,110 A | 11/1996 | Matsen, III et al. | |
| 5,667,512 A | 9/1997 | Johnson | |
| 5,669,145 A | * 9/1997 | Skripsky | 30/371 |
| 5,735,866 A | * 4/1998 | Adams et al. | 606/178 |
| 6,077,270 A | 6/2000 | Katz | |
| 6,272,757 B1 | * 8/2001 | Roe | 30/377 |
| 6,277,121 B1 | 8/2001 | Burkinshaw et al. | |
| 6,302,406 B1 | * 10/2001 | Ventura | 279/48 |
| 6,656,186 B2 | * 12/2003 | Meckel | 606/82 |

* cited by examiner

*Primary Examiner*—Pedro Philogene
*Assistant Examiner*—David A Bonderer

(57) ABSTRACT

A kit (10) for resection of bone (12) for use in implantation of a joint prosthesis (14) is provided. The kit (10) includes a guide (16), a tool (26) and a stop (32). The guide (16) defines an opening (20) through the guide (16). The guide (16) is in cooperation with the bone (12). The tool (26) may be constrained within the opening (20) of the guide (16). The tool (26) includes a cutting edge (30) for resection of bone (12). The stop (32) cooperates with the guide (16) and the tool (26) to limit the movement of the tool (26) within the guide (16) so that the position of the cutting edge (30) with respect to the bone (12)m may be controlled. The stop (32) includes a plurality of positions (34) with respect to the tool (26) and the guide (16).

16 Claims, 15 Drawing Sheets

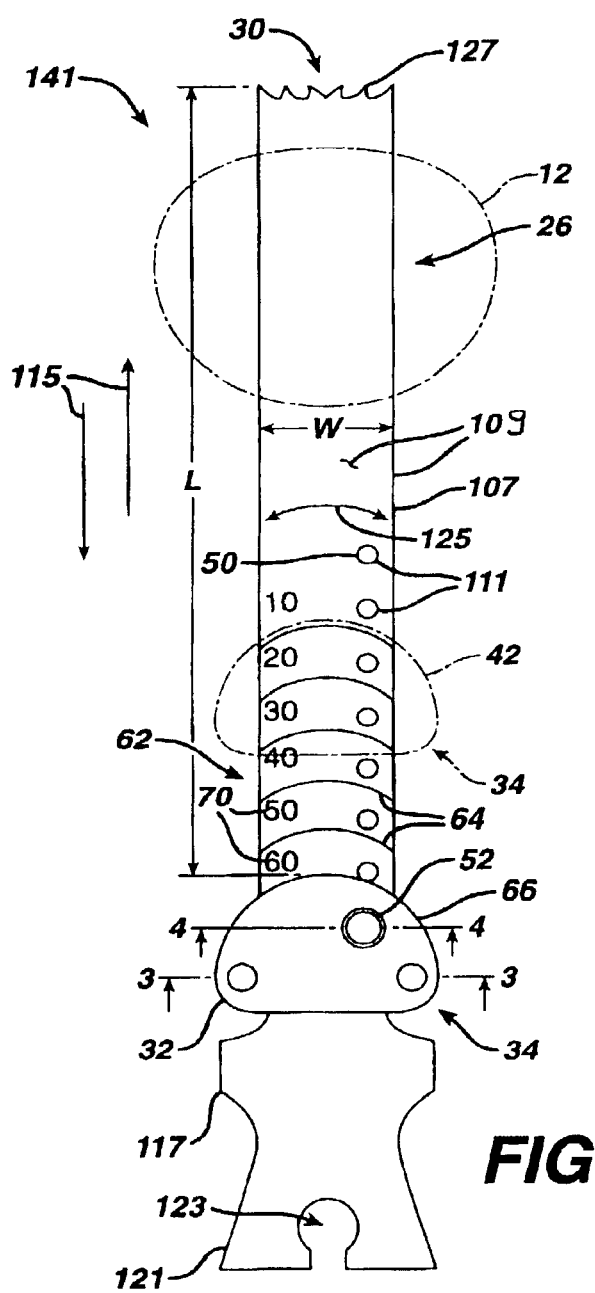
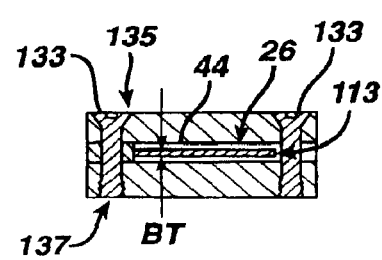
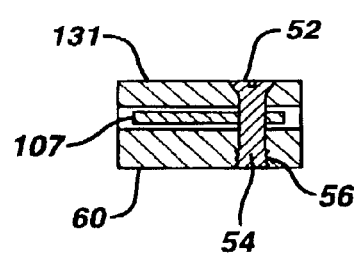
FIG. 2
FIG. 3
FIG. 4

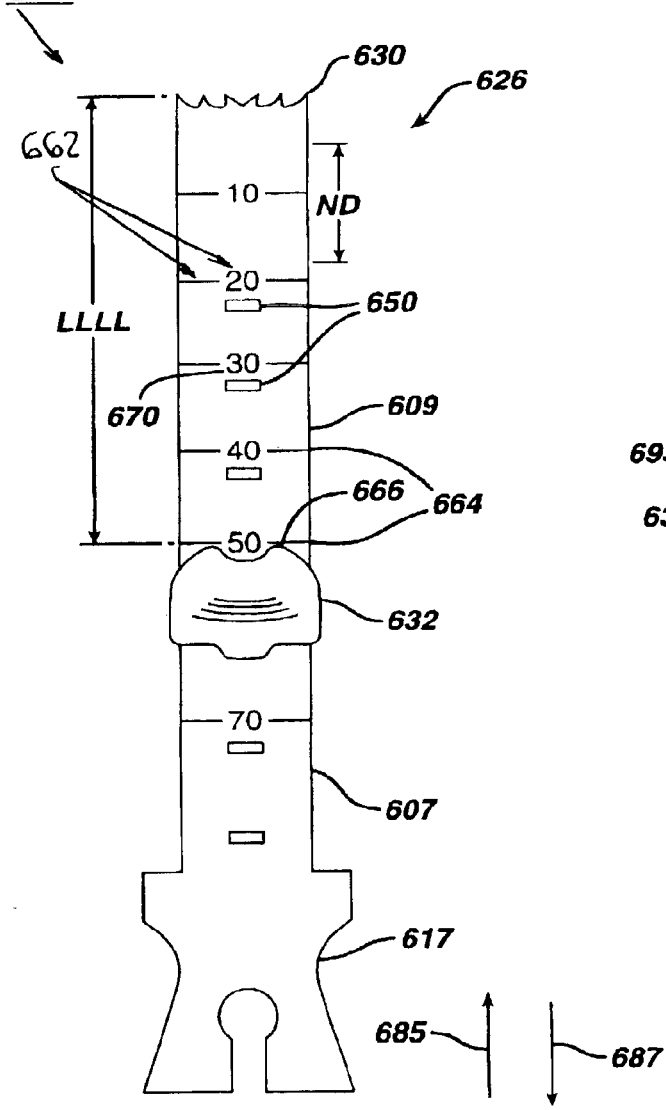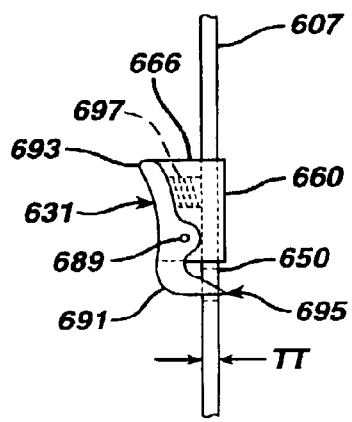
FIG. 16
FIG. 17

BLADE FOR RESECTION OF BONE FOR PROSTHESIS IMPLANTATION, BLADE STOP AND METHOD

CROSS REFERENCE TO U.S. PROVISIONAL PATENT APPLICATION

This application is a Utility Patent Application based upon U.S. Provisional Patent Application Ser. No. 60/363,528 filed Mar. 12, 2002, entitled BLADE FOR RESECTION BONE OF PROSTHESIS IMPLANTATION, BLADE STOP AND METHOD.

TECHNICAL FIELD OF THE INVENTION

The present invention relates generally to the field of orthopedics, and more particularly, to an implant for use in arthroplasty.

BACKGROUND OF THE INVENTION

Joint replacement surgery is quite common and it enables many individuals to function properly when otherwise it would not be possible to do so. Such patients of joint replacement surgery typically suffer from osteoarthritis or rheumatoid arthritis. Artificial joints usually comprise metallic, ceramic and/or plastic components that are fixed to existing bone.

Such joint replacement surgery is otherwise known as total joint arthroplasty. Total joint arthroplasty is a well known surgical procedure by which a diseased and/or damaged joint is replaced with a prosthetic joint. In a typical total joint arthroplasty, the ends or distal portions of the portion of the bone adjacent the joint are resected or a portion of the distal part of the bone is removed and the artificial joint is secured thereto. Often, particularly in knee and hip total joint arthroplasty, the distal portion of the bone is resected and the medullary canal exposed. The components of the prosthesis often include stems that are fitted into the exposed medullary canal.

Often, and particularly in, for example, knee, shoulder, or ankle total joint arthroplasty, instruments in the form of bone resecting tools are often utilized with guide blocks to provide for accurate bone resection. The joints are positioned frequently with respect to the resected surfaces of the bones and therefore the accuracy of their placement is important. Often, these guide blocks include elongated slots that are utilized to guide an oscillating saw blade.

When sawing through a saw block with an oscillating saw, it is difficult to control the depth of the cut. Fragile soft tissue in the form of, for example, tendons, ligaments, vascular and neurological structures, and muscle surround and are secured to the bone. When utilizing an oscillating saw to resect bone, as the saw penetrates completely through the bone, the force required to cut through the hard bone may cause the saw to lunge forward toward the soft tissue. The protection of the tendons, ligaments, and muscles adjacent the bone when the oscillating saw is exiting the bone is crucial.

Marks have been placed on the saw blades to assist in the controlling of the depth of the cut when using an oscillating saw. For example, blade manufactures have put marks such as position indicators in the form of scales on their products to give their users a visual representation of how deep they are cutting. Such scales do not actually stop the blade from cutting too deep and damaging soft tissue, ligaments or tendons.

The use of oscillating saws with cutting blocks having elongated slots are widely used in total joint arthroplasty. Such combinations of oscillating saws and cutting blocks are frequently used in total knee arthroplasty and, for example, in total ankle arthroplasty.

An example of the situation of making a cut utilizing an oscillating saw in a cutting block is the surgical procedure for the DePuy Agility™ ankle tibial component. Before the Agility™ ankle tibial component may be inserted, the distal end of the tibia and fibula must be resected. This resection is done through an anterior approach through a mounted saw block. On the opposite side of the tibia and fibula are a neurovascular bundle and the Achilles tendon. A need therefore remains for an invention to control the depth of an oscillating saw when resecting bone, particularly for use in knee and ankle arthroplasty.

SUMMARY OF THE INVENTION

According to the present invention, a surgical saw blade for use with an oscillating saw is provided with an adjustable stop. The stop is movable along the length of the surgical blade. The stop may, for example, slide up and down the blade. The stop may have preset positions along the blade in, for example, five (5) millimeter increments. The blade may include a feature to provide for quick release of the stop from the blade to make the positioning of the stop along the blade easier and quicker. The surgical blade with the adjustable stop is designed to control the depth of cut of resected bone through its cooperation with the opening of a mating saw block.

The surgical blade according to the present invention, may be made of any suitable, durable material and may be made, for example, of stainless steel. The blade may include an adapter end for cooperation with a commercially available oscillating saw. For example, the blade adapter may be such to cooperate with a commercially available Stryker oscillating saw utilizing the Stryker adapter design. The stop may have a biased stop release with an ability to positively lock and limit motion of the blade outwardly.

The stop may have a round front face that represents the arc of the oscillating motion. The blade also may have a scale that starts at the cutting edge in ten (10) millimeter increments from, for example, forty (40) to eighty (80) millimeters. Alternatively, the blade may have other increments, for example, five (5) millimeter increments. The scale markings on the blade may be in arcuate shapes that match the rounded face of the stop.

The present invention may be in the form of an instrument set or kit including the surgical blade with the stop, a saw block, as well as, possibly, a depth gauge.

The present invention may include special surgical techniques utilizing the saw blade with adjustable stop of the present invention. An example of the special surgical technique for this device may be as follows. First, mount a saw block to the distal end of the tibia and fibula. Drill through the saw block, anterior cortex and posterior cortex of the tibia. Next, take a depth gauge and measure through the saw block and tibia. One should make sure to hook on the posterior cortex of the tibia for the depth reading. Push the button on the stop of the blade and slide it to the same measurement just taken by the depth gauge. Next, place the blade in the saw and make the resection through the saw block. The cut can be made with much more accuracy and confidence utilizing this device.

According to one embodiment of the present invention, there is provided a kit for resection of bone for use in implantation of a joint prosthesis. The kit includes a guide, a tool and a stop. The guide defines an opening through the guide. The guide is in cooperation with the bone. The tool may be constrained within the opening of the guide. The tool includes a cutting edge for resection of bone. The stop cooperates with the guide and the tool to limit the movement of the tool within the guide so that the position of the cutting edge with respect to the bone may be controlled. The stop includes a plurality of positions with respect to the tool and the guide.

According to another embodiment of the present invention there is provided a guide for guiding a tool having a stop for use in bone for preparation of a bone cavity for implantation of a joint prosthesis. The guide is adapted for cooperation with the bone. The guide defines an opening through the guide. The guide constrains the tool within the opening of the guide. The guide cooperates with the stop and the tool to limit the movement of the tool within the guide so that the position of the cutting edge with respect to the bone may be controlled. The guide has a plurality of positions with respect to the tool and the guide whereby the guide provides for a plurality of cutting positions of the tool with respect to the bone.

According to yet another embodiment of the present invention there is provided a tool for resection of bone for use in preparation of a cavity for implantation of a joint prosthesis. The tool cooperates with a tool stop and fits within an opening of a tool guide in cooperation with the bone. The tool includes a body defining a periphery of the tool. A portion of the body is constrainable within the opening of the guide. The tool also includes a cutting edge adapted for resection of bone and positioned along a portion of the periphery of said body. The tool also includes a plurality of position features associated with the body. The position features are cooperable with the guide and the stop for limiting the movement of the tool within the guide so that the position of the cutting edge with respect to the bone may be controlled.

According to yet another embodiment of the present invention there is provided a tool assembly for resection of bone for use in preparation of a cavity for implantation of a joint prosthesis. The tool fits within an opening of a tool guide in cooperation with the bone. The tool assembly includes a body, a cutting edge and a stop. The cutting edge extends from a first end of the body. The cutting edge is adapted for resection of bone. The stop cooperates with the body and the guide to limit the movement of the body within the guide so that the position of the cutting edge with respect to the bone may be controlled. The stop adapted for having a plurality of stop positions with respect at least one of the body and the guide. The body is constrained within the opening of the guide. The body cooperates with the guide and the stop for limiting the movement of the body within the guide so that the position of the cutting edge with respect to the bone may be controlled. The body has a plurality of positions with respect to the stop and the guide. The body having a plurality of position features for assisting in positioning the stop in one of the stop positions.

According to a further embodiment of the present invention, there is provided a method for implanting a prosthesis onto a bone of a patient. The method includes the steps of making an incision on the patient to expose a portion of the bone of the patient, providing a guide for assisting in implanting the prosthesis, placing the guide against the portion of the bone, measuring the guide and the bone, determining the desired depth of the cut on the bone to prepare the bone for the prosthesis based on the measuring of the guide and the bone. The method also includes the step of providing a tool to make a cut on the bone, the tool adapted to cooperate with the guide and having a stop which is positionable at a plurality of positions along the tool. The method further includes the steps of adjusting the stop to correspond to the desired position of the cut, placing the tool in cooperation with the guide and the bone, forming a mounting surface on the bone with the tool, and attaching the prosthetic component onto the mounting surface.

The technical advantages of the present invention include the ability to guarantee the depth of cut through any saw blade. For example, the adjustable stop of the blade of the present invention when used in conjunction with a mating saw block, can positively limit and accurately set the depth of cut for a resection utilizing the present invention.

The technical advantage of the present invention also includes the ability to use fewer instruments in an instrument set. For example, according to the present invention, the stop on the blade may be adjusted. Thus a blade may be utilized having many different stops. An alternative approach may have been to provide for a series of blades, each blade having a different fixed stop. Utilizing a system with blades having various different stops, require a large number of blades to be included in the instrument set.

The technical advantage of the present invention also includes the ability to lessen the number of other instruments in, for example, the form of retractors that may otherwise be required to be used to protect the anatomy from saw cuts. For example, retractors are used between the saw and critical elements of soft tissue, for example, in total ankle arthroplasty, the Achilles tendon. The adjustable stop of the surgical blade of the present invention used in conjunction with a saw block will provide for an accurate depth of cut, such that the use of retractors to protect soft tissue may not be necessary.

The technical advantage of the present inventions may also include the ability of the stop to not catch the edge of the saw block. This feature is provided by providing the stop with a round front face that represents the arc of the oscillating motion.

According to another aspect of the present invention, the stop may slide up and down the blade providing for easy adjustment of the stop. Further, the stop may feature for quick release of the stop at each position of the blade.

By providing the scaled hash marks, the position of the stop on the surgical blade can be very easily determined.

The technical advantage of the present inventions also include the use of accurate optimum stop measurements that may be patient specific by utilizing the depth gauge to measure the hole made during the surgical procedure.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 2 is a top view of the blade assembly of FIG. 1 including a moveable stop for resecting bone;

FIG. 3 is a cross sectional view of FIG. 2 along the lines 3—3 in the direction of the arrows;

FIG. 4 is a cross sectional view of FIG. 2 along the lines 4—4 in the direction of the arrows;

FIG. 16 is a top view of a blade assembly including an adjustable stop for resecting bone for preparation of a total joint prosthesis implantation in accordance with a further embodiment of the present invention;

FIG. 17 is an end view of the blade assembly of FIG. 16;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
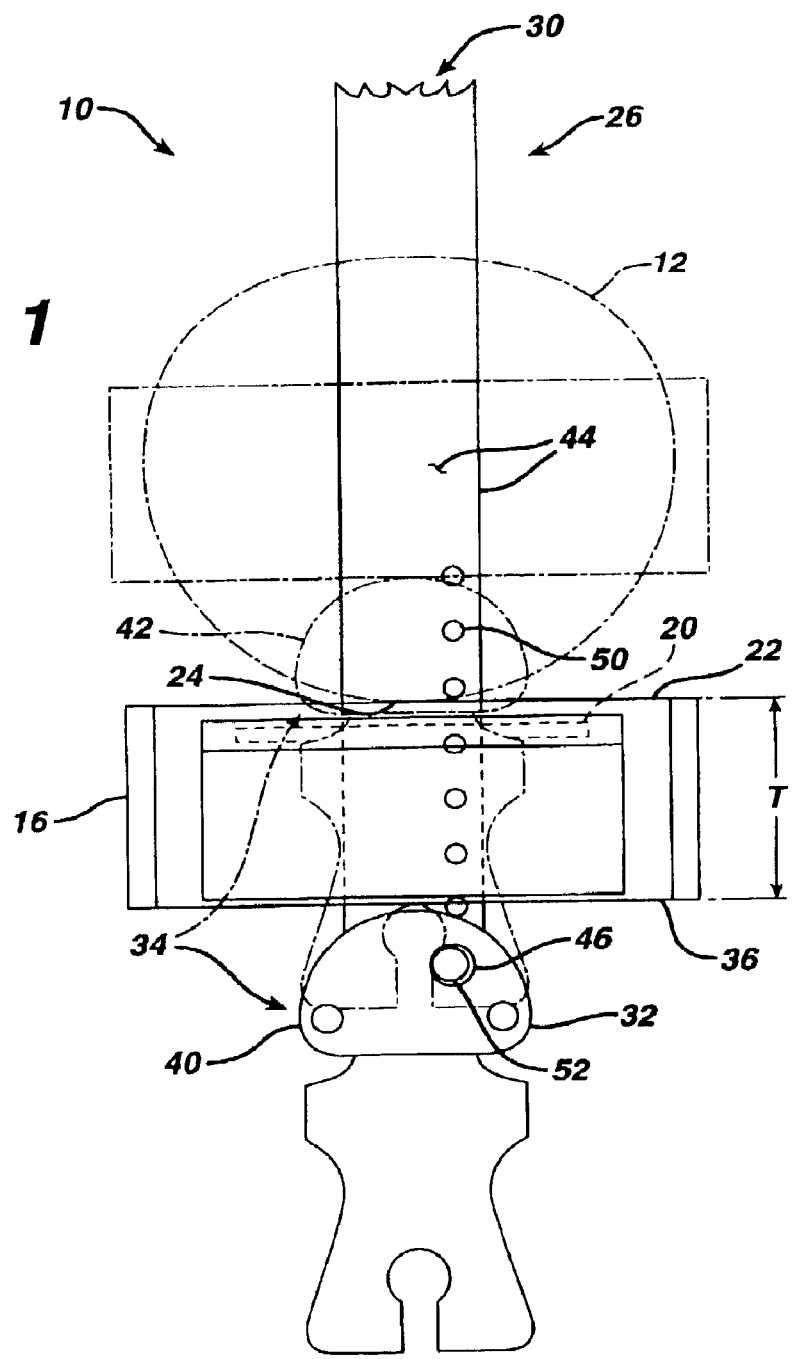
FIG. 1 is a top view of a blade assembly including a moveable stop for resecting bone for preparation of a total joint prosthesis implantation in accordance with an embodiment of the present invention showing a second position of the stop in phantom and showing a cutting block in both a first and a second position.

According to the present invention and referring to FIG. 1, a kit 10 is shown. The kit 10 is utilized for resection of bone 12 to prepare the bone 12 for the implantation of a joint prosthesis 14 (see FIG. 9). The kit 10 includes a guide 16.

The guide 16 defines an opening 20 through the guide 16. The guide 16 is in cooperation with the bone 12, for example and as shown in FIG. 1, the guide 16 includes a first surface 22 which is in contact with surface 24 of bone 12. The kit 10 further includes a tool 26.

Figure 5:
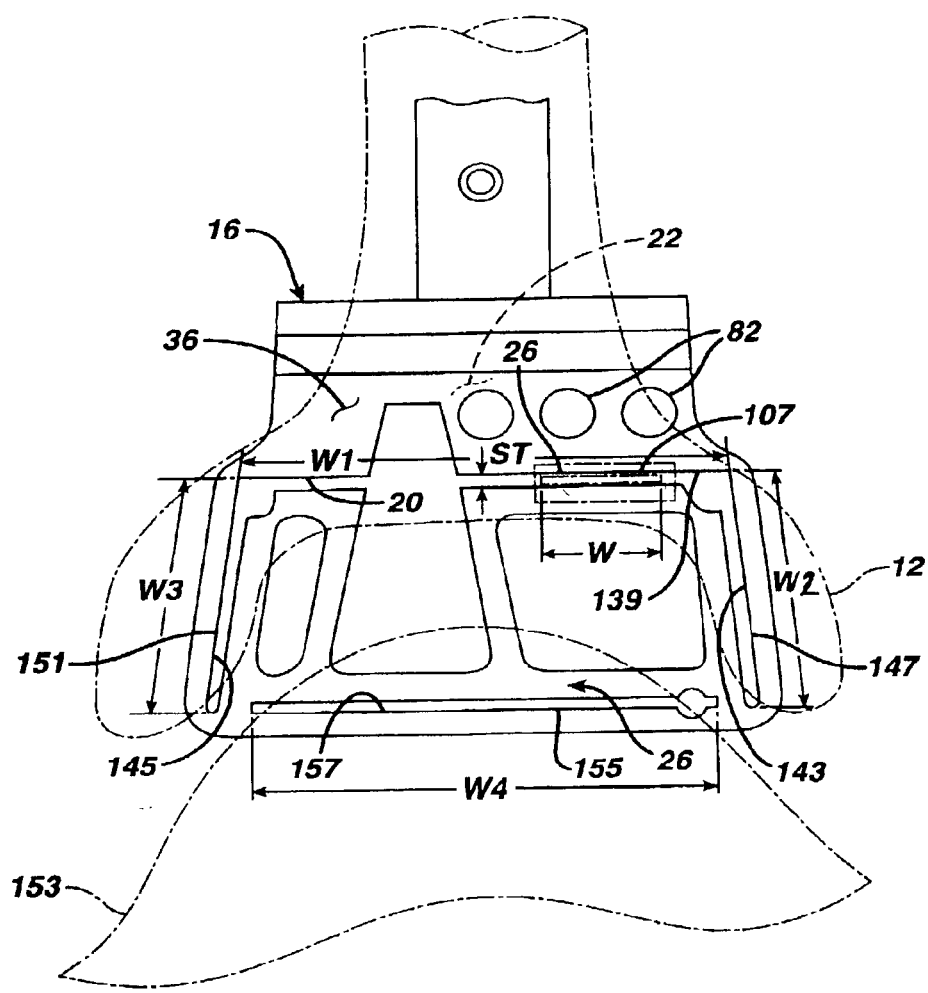
FIG. 5 is a plan view of an ankle arthroplasty cutting block for use with the blade assembly of FIG. 1.

Referring now to FIG. 5, the tool 26 is constrainable within the opening 20 of the guide 16. Referring again to FIG. 1, the tool 26 includes a cutting edge 30 adapted for resection of bone 12.

The kit 10 further includes a stop 32 cooperable with the guide 16 and the tool 26 for limiting the movement of the tool 26 within the guide 16 so that the position of the cutting edge 30 with respect to the bone 12 may be controlled. The stop 32 has a plurality of positions 34 with respect to the tool 26 and the guide 16.

The kit 10 may include a guide such as guide 16 of FIG. 1 which defines a first surface 22 for cooperation with the bone 12 as well as a second surface 36. The second surface 36 may be spaced from the first surface 22 and be adapted to cooperate with the stop 32. For example, and as shown in FIG. 1, the second surface 36 of the guide 16 is spaced from first surface 22 a distance T and as shown in FIG. 1, the second surface 36 may be parallel to first surface 22.

Referring now to FIG. 5, the opening 20 of the guide 16 may be in the form of a slot. The tool 26 may be in the form of a blade. The blade 26 may slide within the opening 20.

Referring again to FIG. 1, the stop 32 may be slidably positioned along tool 26 and be permitted to move from, for example, a first stop position 40 to a second stop position 42 as shown in phantom.

Referring now to FIGS. 3 and 4, the stop 32 may surround at least a portion of the tool 26. For example, as shown in FIGS. 3 and 4, the stop 32 surrounds generally entire periphery 44 of the blade or tool 26.

Referring again to FIG. 1, the stop 32 may include a stop feature 46. The tool 26 may include a plurality of tool features 50. Each of the tool features 50 may correspond to one of the said plurality of stop positions 34 along the tool 26.

The stop feature 46 may be in the form of an aperture in the stop 32. Similarly, the tool features 50 may be in the form of apertures in the tool 26. When the stop feature 46 is in the form of an opening and the tool feature 50 is in the form of an opening as shown in FIG. 1, the stop feature 46 and tool feature 50 may be aligned and secured to each other by one of a series of features. For example, a pin 52 may be utilized to interconnect the stop 32 to the tool 26 at the stop aperture or opening 46 and at one of the tool features or tool openings 50.

Referring now to FIG. 3, the pin 52 may be secured to the stop 32 in any suitable way. For example, the pin 52 may include external threads 54 which mate with internal threads 56 on bottom portion 60 of the stop 32. It should be appreciated that alternatively, the internal threads which mate with external threads on the pin 52, may be formed in holes 50 in the tool or blade 26. It should be appreciated that the pin 52 may be secured in position by interference fit (not shown). Any other suitable way may be used to secure the pin 52.

As shown in FIG. 2, the blade 26 or stop 32 may include indicia 62 thereon which indicia correspond to one of the stop positions 42. For example and as shown in FIG. 2, the indicia 62 are maybe located on the blade 26. The indicia 62 may be in the form of lines or scale hash markings 64. As shown in FIG. 2, the scale hash markings 64 may be in an arch shape that matches arcuate face 66 of the stop 32. The markings 64 may be applied by paint, etching, forming or any method capable of providing markings that are visual. The markings 64 serve to assist in the proper alignment of the stop 32 to the respective positions 34 along the blade 26.

The indicia 62 may also include numbers 70 which correspond to the distance L from face 66 of the stop 32 to cutting edge 30 of the blade 26. The numbers 70 may be painted, etched, engraved or stamped into the blade 26. The numbers 70 are preferably placed slightly above the corresponding marking 64.

Figure 8:
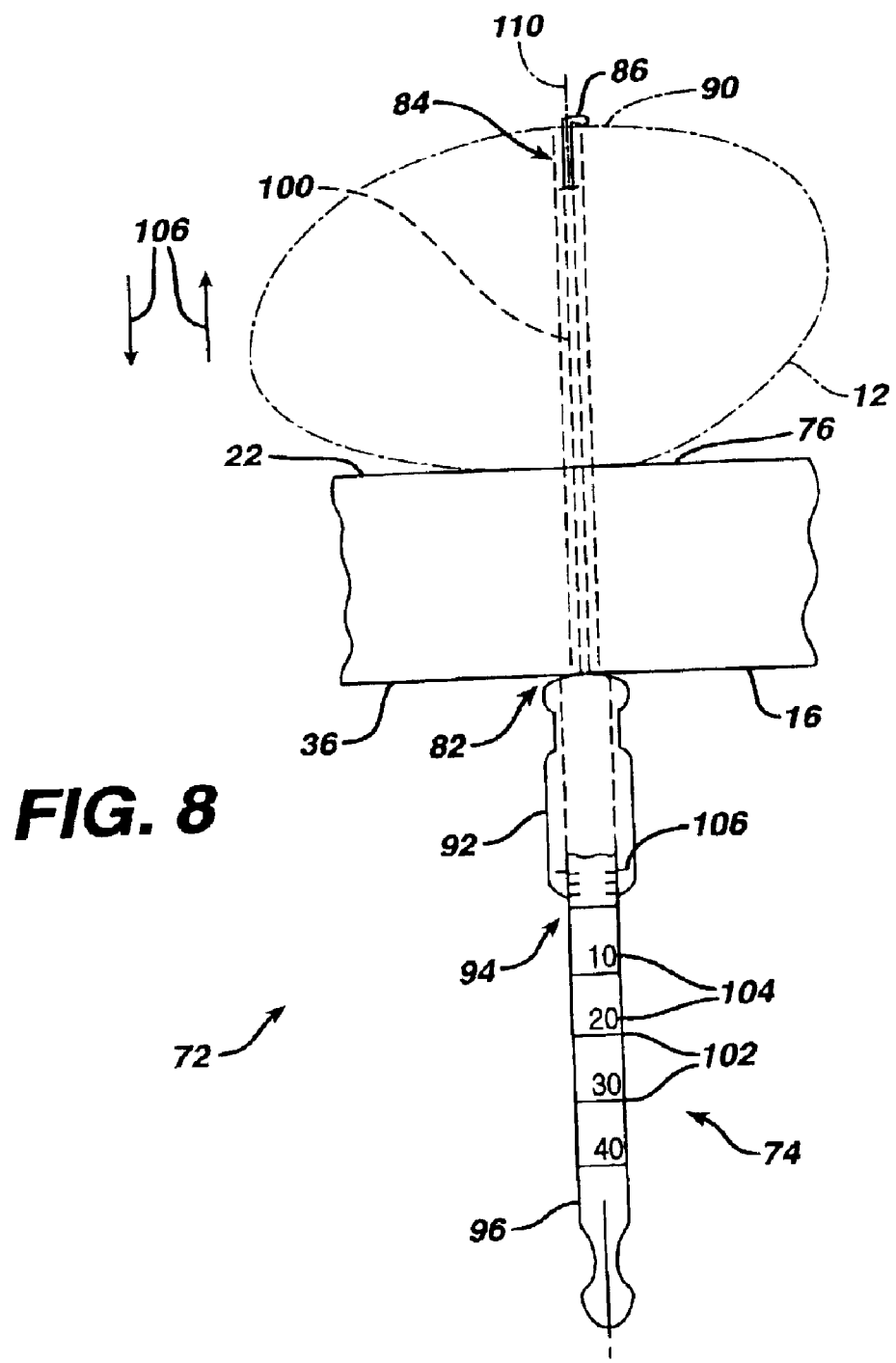
FIG. 8 is a plan view of a depth gage for use in setting the stop of the blade assembly of FIG. 1.

While the kit of the present invention may as shown in FIG. 1, include the tool 26, the stop 32 and the guide 16, the kit 10 may additionally include a gauge 72 as shown in FIG. 8.

Referring to FIG. 8, the gauge 72 is utilized for determining the proper position of the stop 32 with respect to the tool 26 (see FIG. 1). The gauge 72 includes indicia 74 located on the gauge 72 which indicia 74 correspond to the positions 34 of the tool 26.

As shown in FIG. 8, the gauge 72 is utilized by first placing guide 16 against anterior cortex 76 of the bone 12, for example, tibia 12. A drill or cutting tool (not shown) is positioned in through hole 82 and machines an opening 84 through the tibia 12. The gauge 72 is positioned into through hole 82 and into opening 84. A hook 86 on the gauge 72 then engages posterior cortex 90 of the tibia 12.

The gauge 72 may have any suitable shape and may, for example, include a body 92 which is sized to slidably fit within through hole 82 of guide 16. The body 92 may include a body opening 94. Stem 96 and wire 100 are coaxially slidably mounted within the body opening 94.

The indicia 74 on the gauge 72 may be painted, stamped, etched or provided by any suitable method. The indicia 74 may include a plurality of lines 102 and numbers 104 placed along the length of the stem 96. An alignment mark 106 may be placed on the body 92 for aligning the lines 102 with the mark 104.

In utilizing the gauge 72, the hook 86 is placed in contact with the posterior cortex 90 by moving the stem 96 in the direction of arrows 106 along axis 110 of the body 92. When the hook 86 is in contact with the posterior cortex 90, the number 104 of the stem of the gauge 72 corresponding to the proper position 34 of the stop with respect to the tool 26 (see FIG. 1) is determined by reading the number 104 positioned adjacent the mark 106 on the stem 96 of the gauge 72. This number will correspond to the number 70 at which the stop 32 should be positioned to properly place the stop 32 along the blade 26 so that the cutting edge 30 of the blade 26 will barely reach posterior cortex 90 of the tibia 12.

Referring now to FIGS. 2 through 4, the tool 26 is shown in greater detail.

Referring to FIGS. 1 through 4, the tool 26 is shown in greater detail. The tool 26, as shown in FIGS. 1 through 4, include a body 107. The body 107 defines a periphery 109 thereof. The tool 26 also includes the cutting edge 30. The cutting edge 30 is positioned along a portion of periphery 109 of the body 107.

Referring now to FIG. 5, at least a portion of the body 107 is constrainable within the opening 20 of the guide 16.

Referring again to FIGS. 1 through 4, the tool 26 further includes a plurality of position features 50 which are associated with the body 107. For example, as shown in FIGS. 1 and 2, the body 107 defines a plurality of tool apertures 111. The tool apertures 111 correspond to the position features 50.

The body 107 may have any suitable shape which is compatible with opening 20 of the guide 16 (see FIG. 5). For example, the body 107 may be in the form of a planer blade having a length L and a width W. The width W is preferably generally constant along the length L of the blade 107 such that the blade 26 may be accurately guided within opening 20. The blade 107 may have a blade thickness BT of a size suitably fitted for the opening 20. For example, the body 107 may have a thickness BT of, for example, 0.2 to 0.8 inches. For example, the blade may have a thickness of around 0.035 inches.

Referring to FIGS. 2 through 4, the stop 32 may define an opening 113 therein. The opening 113 is sized such that the body 107 may slide longitudinally in the direction of arrows 115.

The tool 26 may further include a hub 117 which extends outwardly from body 107 of the tool 26. The hub 117 cooperates with oscillating tool (not shown). The hub 117 includes locating features in the form of, for example, tabs 121 and opening 123. The tabs 121 and opening 123 correspond with mating features on the oscillating tool to permit securement of the tool 26 to the oscillating tool.

The oscillating tool may be any power tool utilized to provide for oscillation of the tool 26 in the direction of arrows 125. For example, the oscillating tool may be a standard oscillating tool provided by Stryker/Howmedica, Osteonics. The tabs 121 and opening 123 for hub 117 as shown in FIGS. 1 and 2, are generally adaptable to a Stryker oscillating tool. It should be appreciated that an oscillating tool from another supplier may be equally suitable to this invention. For example, the oscillating tool may be in the form of an oscillating tool from Linvatec, an operating company of ConMed.

The body 107, cutting edge 30 and hub 117 may be, as shown in FIGS. 1 and 2, integral. The body 107, cutting edge 30 and hub 117 may be made of any suitable, durable material, for example, stainless steel, tool steel, and other material that may be sterilizable.

The cutting edge 30 may have any shape suitable for resection of bone 12. For example, the cutting edge 30 may include a plurality of teeth 127. The teeth 127 may be each of similar size and shape or may, as shown in FIGS. 1 and 2, have a variety of shapes and orientations. The size and shape of the teeth 127, as shown in FIGS. 1 and 2, are indicative of a Synvasive blade.

Referring to FIGS. 1 through 4, the stop 32 may have any suitable shape and preferably includes the face 66 which is arcuate for permitting oscillation of the body 107 in the directions of arrows 125. The stop 32 may have any suitable construction and typically includes a top portion 131 which is opposed from bottom portion 60. Body 107 is positioned between the top portion 131 and the bottom portion 60.

While the top portion 131 and the bottom portion 60 may be integral with each other, as shown in FIGS. 1 through 4, the top portion 131 and the bottom portion 60 are made of separate components. The top portion 131 and bottom portion 60 may be secured to each other in any suitable manner.

For example as shown in FIGS. 3 and 4, top portion 131 may be secured to bottom portion 60 by means of screws 133 which are fitted into openings 135 and 137 in the top portion 131 and bottom portion 60, respectively. The stop 32 may be made of any suitable material. For example, the stop 32 may be made of a durable plastic, for example, polyethylene or be made from a metal, for example, stainless steel. The material from which the stop 32 is made is preferably sterilizable.

Referring again to FIGS. 1 through 4, a tool assembly 141 according to the present invention is shown. The tool assembly 141 includes the body 107 and the cutting edge 30 which extends from the periphery 109 of the body 107. The cutting edge 30 is adapted for resection of bone 12. The tool assembly 141 further includes the stop 32. The stop 32 is cooperable with the body 107 and the guide 16 (see FIG. 5) so that the position of the cutting edge 30 with respect to the bone 12 may be controlled. The stop 32 is adapted for having a plurality of stop positions 34 with respect to at least one of the body 107 and the guide 16.

The body 107 is constrainable within the opening 20 of guide 16 (see FIG. 5). The body 107 is cooperable with the guide 16 and the stop 32 for limiting the movement of the body 107 within the guide 16 so that the position of the cutting edge 30 with respect to the bone 12 may be controlled. The body has a plurality of position features 50 for assisting and positioning the stop 32 in one of the stop positions 34.

Referring now to FIG. 5, the guide 16 is shown in greater detail. The guide 16 includes a first surface 22 as well as a second surface 36 spaced from and generally parallel to first surface 22. The guide 22 serves to provide guidance and positioning for tool 26. The guidance provided by the guide 16 is typically in the form of an opening, for example, first opening 20 in the form of an elongated slot. The slot 20 has a slot thickness ST which is sized to provide clearance with respect to the thickness BT of the blade 26 (see FIG. 3). The guide 16 is positioned such that the first slot 20 is in a position to resected surface 139 of tibia 12.

As shown in FIG. 5, the guide 16 may also be utilized to resect angled surfaces 143 and 145 of the tibia 12. The first opening 20 has a width W1 which generally corresponds to the width of the surface 139 of the tibia 12.

To assist in providing angled surfaces 143 and 145, preferably, the guide 16 includes a second slot 147 and a third slot 151. The second slot and third slot 147 and 151, respectively, have a width similar to the width ST of the first slot 20. The second slot 147 and the third slot 151 have widths W2 and W3, respectively, which correspond to the resected lengths of surfaces 143 and 145, respectively.

The guide 16 may further be utilized to resect talus 153. To resect the talus 153, the guide 16 may include a fourth opening or slot 155. The fourth slot 155 has a width W4 corresponding to the resected width of surface 157 of talus 153. The fourth slot 155, similar to the first, second and third slots 20, 147, and 151, respectively, has a width similar to width ST of surface 139.

Figure 6:
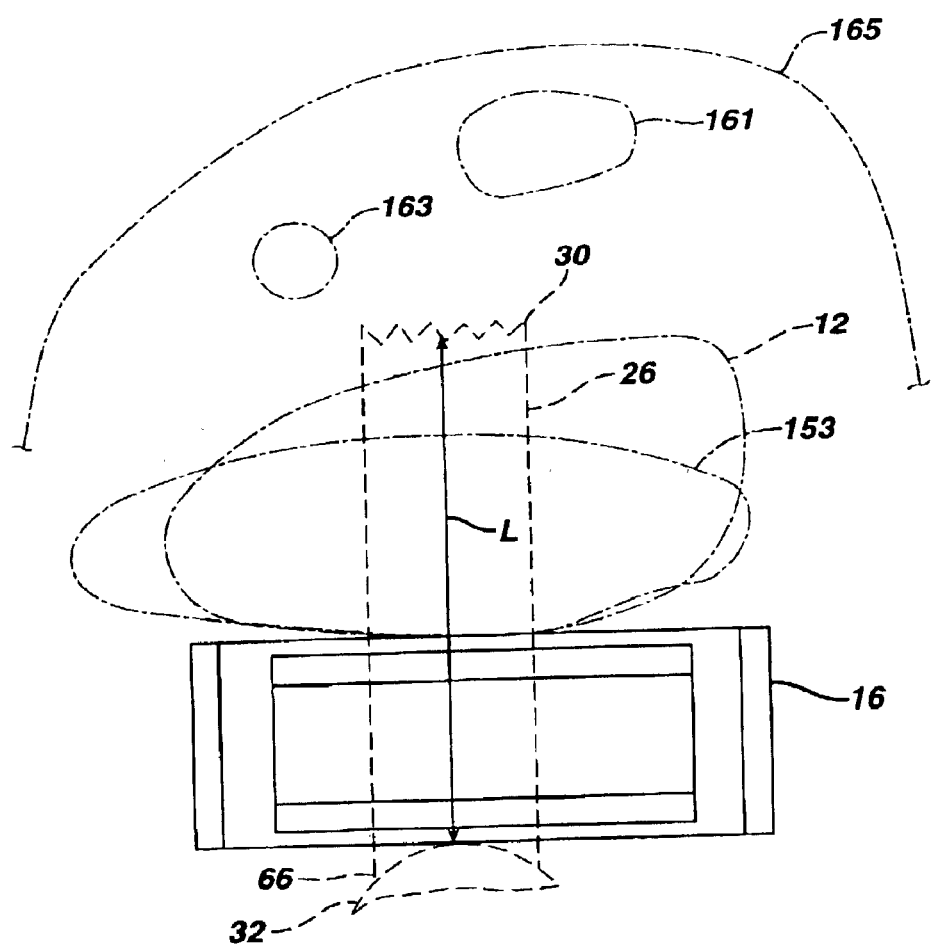
FIG. 6 is a top view of the ankle arthroplasty cutting block of FIG. 5.

Referring now to FIG. 6, the guide 16 is shown with blade 26, tibia 12 and talus 153 in phantom. The blade 26 has an effective cutting length L from surface 66 of stop 32 to cutting edge 30. As can be seen in FIG. 6, the cutting edge 30 of the blade 26 is such that the entire tibia 12 and talus 153 may be resected, while protecting soft tissue 161. Soft tissue 161 may include tendons, ligaments, vascular and neurological structures, and muscle tissue. When resecting portions of the tibia 12 and talus 153, Achilles tendon 163 located posteriorly in calf 165 is particularly vulnerable to cutting edge 30 of the blade 26.

Figure 7:
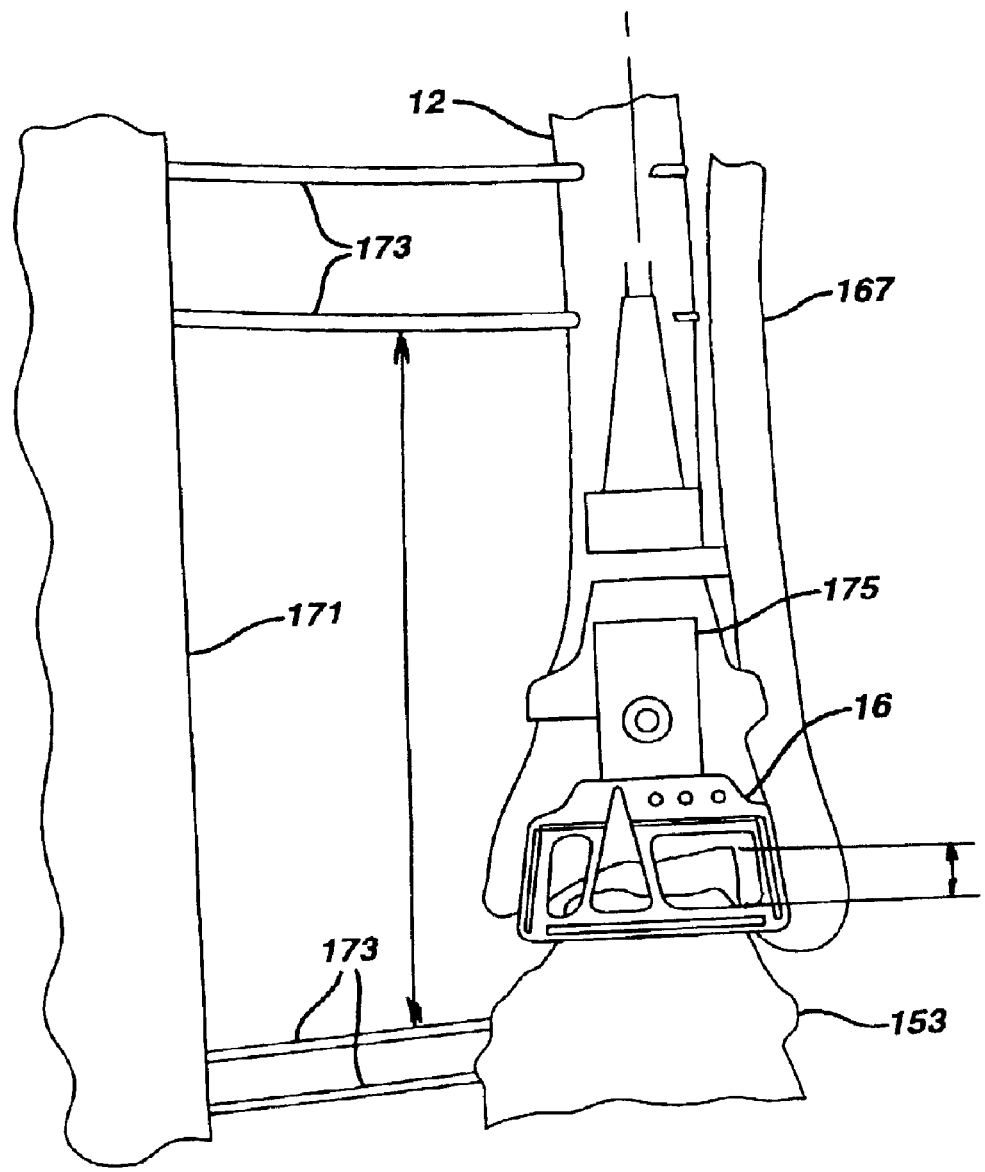
FIG. 7 is a plan view of the ankle arthroplasty cutting block of FIG. 2 mounted in position on a patent.

Referring now to FIG. 7, the guide 16 is shown in position with respect to the tibia 12 and the talus 153. Fibula 167 is also shown adjacent the tibia 12. A joint distractor 171, may be utilized to fixedly position the tibia 12, the fibula 167 and the talus 153 in position for the resecting of the tibia 12 and the talus 153. The joint distractor 171 may include alignment screws 173 which are secured into tibia 12 and talus and calcaneus 153 rigidly positioning the tibia 12 with respect to the talus 153. After the positioning of the tibia 12 with respect to the talus 153, the guide 16 may be securely positioned to the tibia by means of bracket 175.

Figure 9:
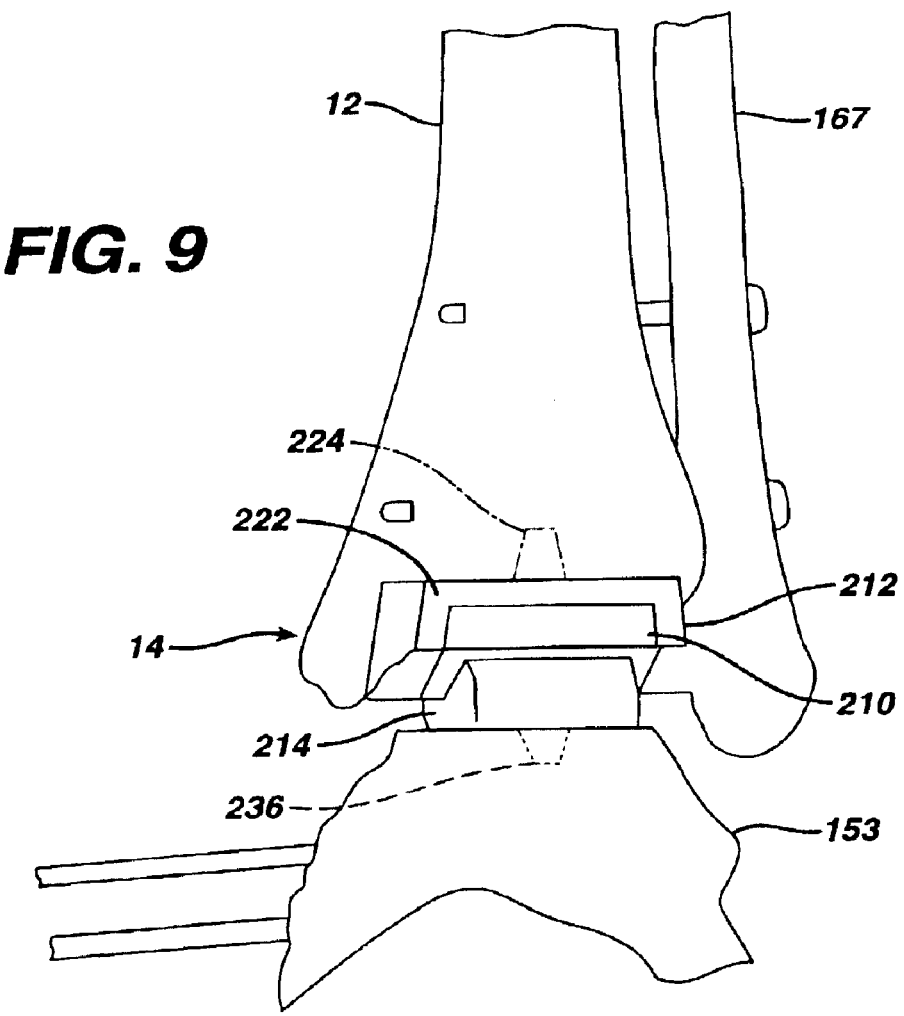
FIG. 9 is a plan view of a total ankle implant installed in a patient which may use the block of FIG. 5 in its installation.

Referring now to FIG. 9, the joint prosthesis 14 is shown implanted into the tibia 12, fibula 167 and talus 153. As shown in FIG. 9, the ankle prosthesis 14 is implanted with talar member 214 attaching to the talus 153 and tibial member 212 attaching to the tibia 12 fibula 167 with base plate 222 bridging the bones. Tibia strut 224 extends up into the tibia 12 when implanted and also positions the tibial member 212 correctly. Bearing 210, typically made of polyethylene, is positioned between tibial member 212 and talar member 214. In a similar matter, talar strut 236 extends down into the talus 153 to keep the talar member 214 properly aligned when implanted. The ankle 14 is preferably attached without cement as the surfaces of the ankle contacting the bones may have a special coating, typically a porous coating to provide for bone in-growth, applied using a surface treatment, for example, micro-beads of metal sintered onto the surface.

Since patients have different ankle size, different size ankle implants 14 may be required. The correct size is obtained by comparing x-rays of each patient's ankle to an outline of each size implant. It has been found that small, medium and large size implants provide sufficient variations to accommodate virtually all replacement situations.

Figure 10:
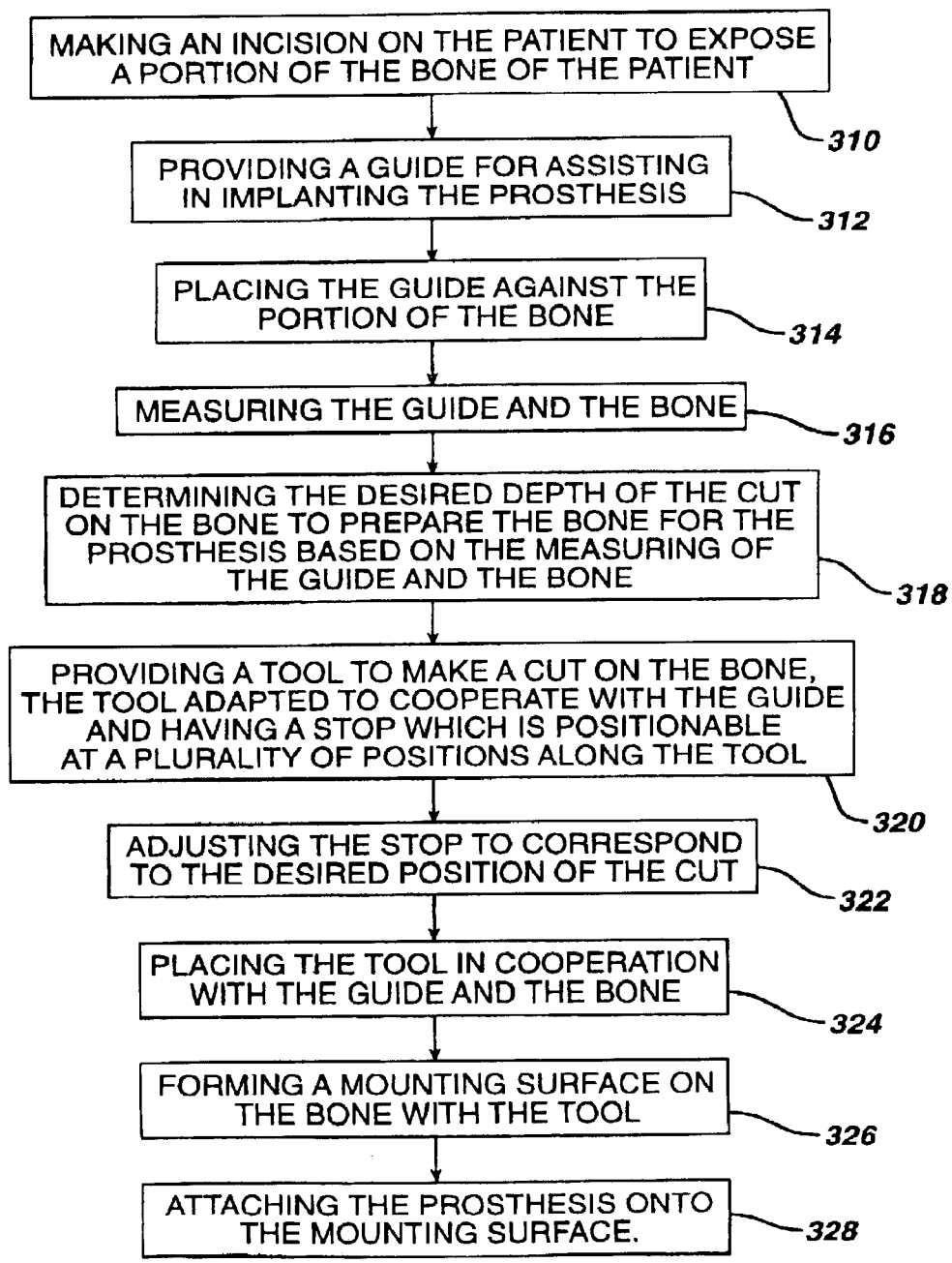
FIG. 10 is a flow chart of a method of performing total joint arthroplasty according to the present invention.

Referring now to FIG. 10, a method for implanting a prosthesis onto a bone of a patient according to the present invention is shown. The for implanting a prosthesis onto a bone of a patient according to the present invention includes a first step 310 of making an incision on the patient to expose a portion of the bone of the patient.

The method further includes the steps of adjusting the stop to correspond to the desired position of the cut, placing the tool in cooperation with the guide and the bone, forming a mounting surface on the bone with the tool, and attaching the prosthetic component onto the mounting surface.

The method further includes a second step 312 of providing a guide for assisting in implanting the prosthesis. The method further includes a third step 314 of placing the guide against the portion of the bone.

The method further includes a fourth step 316 of measuring the guide and the bone. The method of measuring the guide and the bone step may include the steps of using the guide and a cutting instrument to prepare an opening through the bone, providing a measuring instrument, placing the measuring instrument at least partially in the opening, and using the measuring instrument to measure the thickness of the bone and the guide Further, the providing the measuring instrument step may include providing the measuring instrument having measuring instrument marks thereon and the providing the tool step may include providing the tool having tool marks thereon with at least one of the measuring marks corresponding to a tool mark.

The method of arthroplasty further includes a fifth step 318 of determining the desired depth of the cut on the bone to prepare the bone for the prosthesis based on the measuring of the guide and the bone.

The method of joint arthroplasty further includes a sixth step 320 of providing a tool to make a cut on the bone, the tool adapted to cooperate with the guide and having a stop which is positionable at a plurality of positions along the tool.

The method of joint arthroplasty further includes a seventh step 322 of adjusting the stop to correspond to the desired position of the cut. The method of adjusting the stop may include moving the stop along the tool to one of a plurality of defined settings.

The method of joint arthroplasty further includes a eighth step 324 of positioning the tool into the opening of the tool guide.

The method also includes a ninth step 326 of forming a mounting surface on the bone with the tool and a tenth step 328 of attaching the prosthetic component onto the mounting surface.

While the present invention may be practiced with the tool 26 as shown in FIGS. 1 and 2, it should be appreciated that a tool with an adjustable stop may have a large number of possible embodiments. For example, and referring now to FIGS. 11, 12 and 13, cutting tool assembly 441 is shown.

Figure 11:
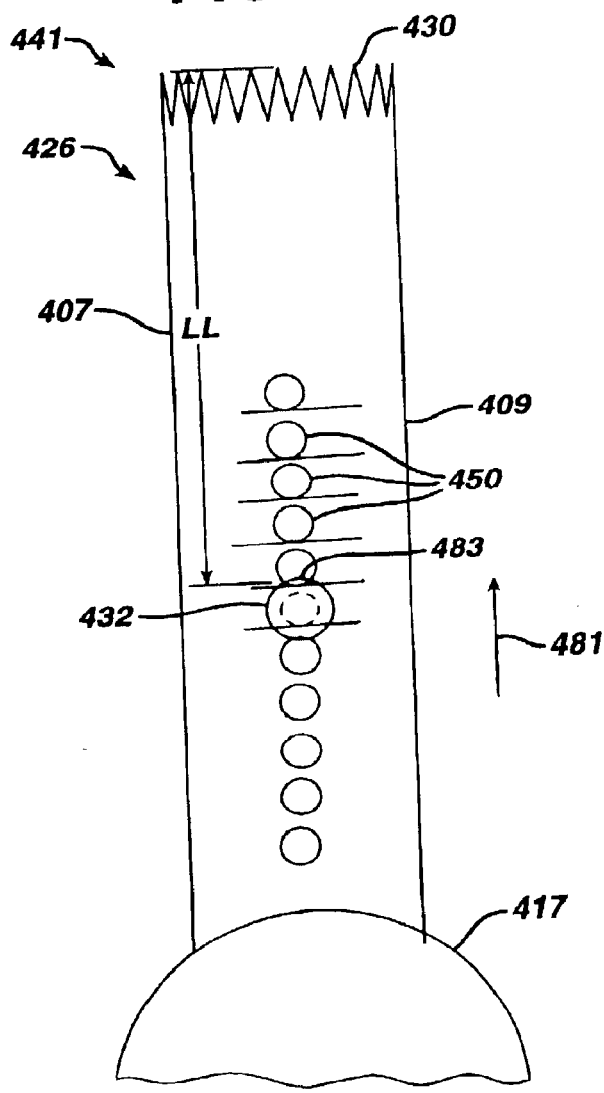
FIG. 11 is a top view of a blade assembly including an adjustable stop in the form of a moveable plug for resecting bone for preparation of a total joint prosthesis implantation in accordance with another embodiment of the present invention.

The tool assembly 441 is similar to tool assembly of 141 of FIGS. 1 through 4. The tool assembly 441 includes body 407 as shown in FIG. 11 in the form of a blade. The blade 407 is similar to blade 107 of the tool assembly 141. The tool assembly 441 further includes cutting edge 430 which is similar to cutting edge 30 of the tool assembly 141. Cutting edge 430 extends from periphery 409 of the blade 407.

The tool assembly 441 further includes a stop 432. The stop 432 is considerably different from stop 32 of the tool assembly 141. Stop 432 is in the form of a plug. The plug 432 includes a central portion 477, as well as end portions 479. The central portion 477 has a diameter, for example, DS which matingly fits within diameter DH of holes 450. The end portions 479 of the plug 432 have a diameter DL which is significantly larger than diameter DH of the holes 450. The end portions 479 serve to secure the plug 432 within the holes 450 and the end portions 479 provide a positive stop to limit the motion of the cutting edge 430 in the direction of arrow 181. Surface 483 of the end portions 479 contacts first surface 22 of the guide 16 (see FIG. 5).

The cutting tool assembly 441 may further include a hub 417 similar to hub 117 of the tool assembly 141. The hub 417 is utilized to secure the body 407 to a reciprocating tool (not shown).

Referring again to FIGS. 11–13, a tool 426 according to the present invention is shown. The tool 426 is similar to tool 26 of FIGS. 1 and 2 and includes the body 407, the position features 450 and the cutting edge 430.

The holes 450 are spaced longitudinally along blade 407 in the direction of arrow 481 and are spaced from each other a distance of, for example, HS. The distance HS is preferably greater than diameter DH to provide for the tool 426 with ample support around the holes 450 to properly secure the stop 432.

The blade 407 is made of any suitable durable material and, for example, may be made of a material similar to blade 107 of the tool assembly 141.

The stop 432 may be made of any suitable durable material and is preferably made of a resilient material, for example, a polymer, capable of contractions such that diameter DL of the end portions 479 may pass through the holes 450 to permit assembly of the stop 432 into the blade 407.

Figure 12:
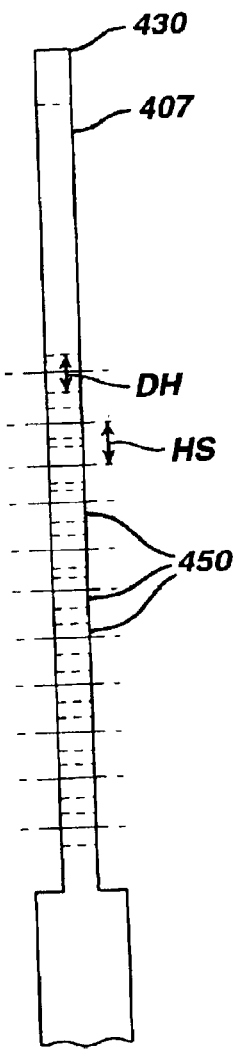
FIG. 12 is an end view of the blade assembly of FIG. 11.
Figure 13:
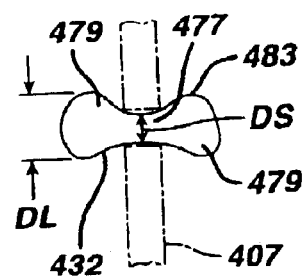
FIG. 13 is a partial end view of the blade assembly of FIG. 11 showing the stop in greater detail.

It should be appreciated, referring to FIGS. 11 through 13, that Length LL from cutting edge 430 to contact surface 483 of the stop 432 may be adjusted by removing the plug 432 from the hole 450 and reinserting the plug 432 in any one of the other of the holes 450 thereby adjusting the length LL.

It should be appreciated that the tool assembly 441 similar to the tool assembly 141 of FIGS. 1 and 2 may include additional features, for example, the indicia lines, numbers (not shown), and any additional feature that may be adapted from the tool assembly 141 and implemented into tool assembly 441.

Figures 14, 15:
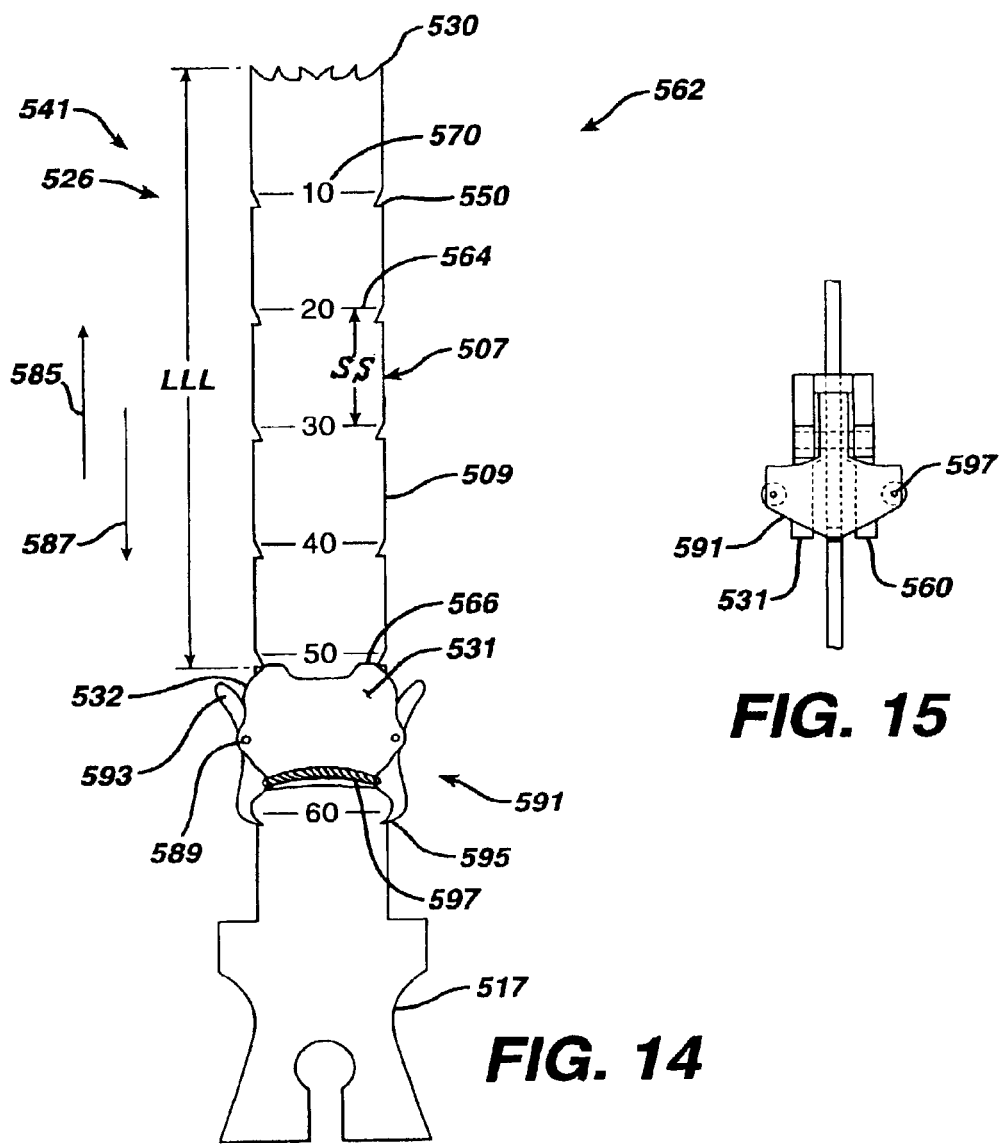
FIG. 14 is a top view of a blade assembly including an adjustable stop for resecting bone for preparation of a total joint prosthesis implantation in accordance with yet another embodiment of the present invention.
FIG. 15 is an end view of the blade assembly of FIG. 11.

Referring now to FIGS. 14 and 15, another embodiment of the present invention is shown as cutting tool assembly 541. The tool assembly 541 includes body 507 in the form of a blade as shown. The cutting tool assembly 541 further includes a cutting edge 530 extending outwardly along periphery 509 of the body 507. The tool assembly 541 further includes a stop 532. While the body 507 and the cutting edge 530 are quite similar to body 107 and cutting edge 30 of the tool assembly 141 of FIGS. 1 and 2, the stop 532 is somewhat different from stop 32 of the tool assembly 141.

According to the present invention and referring again to FIGS. 14 and 15, tool 526 according to the present invention is shown. Tool 526 is similar to tool 26 of FIGS. 1 and 2. Tool 526 includes body 507 and cutting edge 530 which extends outwardly from periphery 509 of the body 507. The tool 526 further includes position features 550. While the body 507 is similar to body 107 of the tool 26 of FIGS. 1 and 2, and while the cutting edge 530 of the tool 526 is similar to cutting edge 30 of FIGS. 1 and 2, the position features 550 are quite different from the position features 50 of FIGS. 1 and 2.

The position feature 550 of FIGS. 14 and 15 are in the form of slots. The slots have a generally bird beak shape or are in a somewhat triangular form to permit the motion of stop 532 freely in the direction of first arrow 585 while limiting motion of stop 532 at the respective slots 550 in the direction of second arrow 587.

The stop 532 of FIGS. 14 and 15 include a top portion 531 as well as a bottom portion 560. At least one of the top portion 531 and the bottom portions 560 include tabs 589 to which palls 591 are pivotally attached. The palls 591 include handles 593 on one end thereof and tips 595 on the opposite ends. The tips 595 are biased in engagement with the slots 550 by, for example, a spring 597. As the handles 593 are moved in toward the body 507, the tips 595 are moved from engagement with the slots 550 to a position spaced from the slots 550. Thus, while the handles 593 are depressed, the stop 532 may be moved in the direction of arrows 587.

By providing the tips 595 and the slots 550 with their triangular shapes and respective orientations, the motion in the direction of arrows 587 is limited such that the gauge 16 (see FIG. 5) when in contact with face 566 of the stop 532 will set a fixed distance LLL between cutting edge 530 and face 566.

The body 507 may be made of any suitable durable material and, for example, may be made of a material similar to that described for body 107 of the tool assembly 141 of FIGS. 1 through 4.

The stop 532 may be made of any suitable material. Top portion 531 and bottom portion 560 of the stop 532 may be made of, for example, a material similar to that of the stop 32 of the tool assembly 141 of FIGS. 1 through 4.

The palls 591 of the stop 532 may be made of any suitable, durable, sterilizable material, for example, a metal or a plastic. The spring 597 may similarly be made of any suitable, resilient durable material and may, for example, be made of a sterilizable metal spring material.

The body 507, may be made similarly to the body 107 of FIGS. 1 through 4, and may include indicia 562 located on periphery 509 of the body 507. The indicia 562 may be in the form of lines 564 or numbers 570. The slots 550 may be positioned from each other along arrows 585 and 587 a distance of, for example, SS of, for example, ten (10) millimeters.

The cutting tool assembly 541 may be mounted to a oscillating tool (not shown) similar as the tool assembly 141 of FIGS. 1 to 4. For example, the body 507 may include a hub 517 similar to hub 117 of the tool assembly 141.

Referring now to FIGS. 16 and 17, yet another embodiment of the present invention is shown as tool assembly 641 (See FIG. 16) Tool assembly 641 includes body 607 in the form of a blade. Blade 607 is similar to blade 107 of the tool assembly 141 of FIGS. 1 through 4. The tool assembly 641 further includes a cutting edge 630 extending along periphery 609 of the body 607. The cutting edge 630 is similar to cutting edge 30 of tool assembly 141 of FIGS. 1 through 4.

Tool assembly 641 further includes a stop 632. Stop 632 is substantially different from stop 32 of the tool assembly 141 of FIGS. 1 through 4.

Referring again to FIGS. 16 and 17, tool 626 according to the present invention is shown. Tool 626 includes a body 607 in the form of a blade. The tool 626 further includes the cutting edge 630. The tool 626 further includes a positioning feature 650. The positioning feature 650 is substantially different from positioning feature 50 of the tool assembly 141 of FIGS. 1 through 4. Positioning feature 650 is in the form of a notch. The notch 650 may be, as shown in FIG. 16, generally rectangular and may merely be an indentation or may extend completely across thickness TT of the blade 607 forming an opening therethrough.

The stop 632, as shown in FIGS. 16 and 17, includes a bottom portion 660 and an opposed top portion 631. The bottom portion 660 includes face 666. The top portion 631 of the stop 632 pivots about pivot point 689 having a pall end 691 opposed in a first direction from the pivot point 689 and a handle end 693 opposed in the opposite direction from the pall end 691. Tip 695 of the pall end 691 is biased into engagement with one of the notches 650 of the blade 607. The pall end 691 has a generally pointed or birds-beak shape such that the stop 632 may slidably move in the direction of arrow 685 freely and such that the tip 695 of the pall end 691 will engage and stop within the notches 650 such that motion in the direction of second arrow 687 is limited to be slidable only between adjacent notches 650.

For example, the pall end 691 may be biased with engagement with the tip 695 in the notch 650 at any various numbers of ways. For example and as shown in FIGS. 16 and 17, a spring 697 may be positioned between handle end 693 of the top portion 631 and the bottom portion 660. The spring 697 serves to bias the pall end 691 with the tip 695 engaged in the notch 650.

By pressing on handle end 693 of the top portion 631 in the direction toward the blade 607, the pall end 691 moves in a direction away from the blade 607 such that the tip 695 is spaced from notch 650 permitting motion of the stop 632 in the direction of arrow 687.

By proper position of the stop 632 along the body or blade 607, the distance LLLL between the cutting edge 630 and face 666 may be adjusted such that when the tool assembly 641 is placed in cutting block 16 (see FIG. 5), the cutting edge 630 may be properly limited in its position.

The tool assembly 641 may further include indicia 662 on the blade 607. The indicia 662 may be in the form of lines 664 or numbers 670. The lines 664 may be separated from each other a distance ND of, for example, 10 millimeters.

The tool assembly 641 may be connected to an oscillating saw (not shown) by any suitable method, for example, by hub 617 similar to hub 117 of the tool assembly 141 of FIGS. 1 through 4.

The blade 607 may be made of any suitable, durable material and may, for example, be made of a material similar to blade 107 of the tool assembly 141 of FIGS. 1 through 4. The stop 632 may be made of any suitable, durable material capable of sterilization. For example, the bottom portion 660 and the top portion 631 of the stop 632 may be made of a plastic, for example, polyethylene. The spring 697 may be made of a material similar to spring 597 of the tool assembly 541 of FIGS. 14 and 15.

Figure 18:
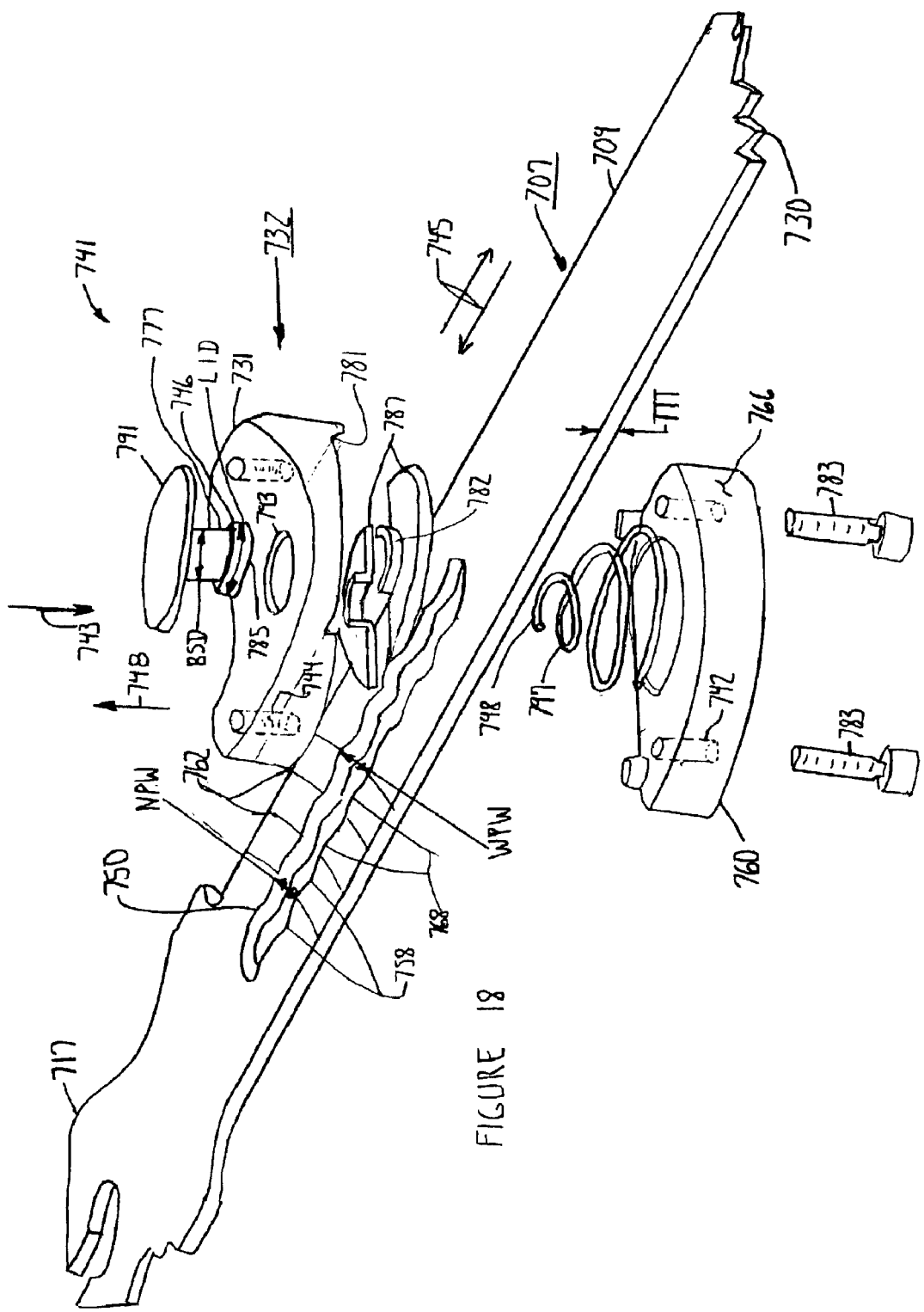
FIG. 18 is an exploded perspective view of a blade assembly including an adjustable stop for resecting bone for preparation of a total joint prosthesis implantation in accordance with a further embodiment of the present invention.
Figure 19:
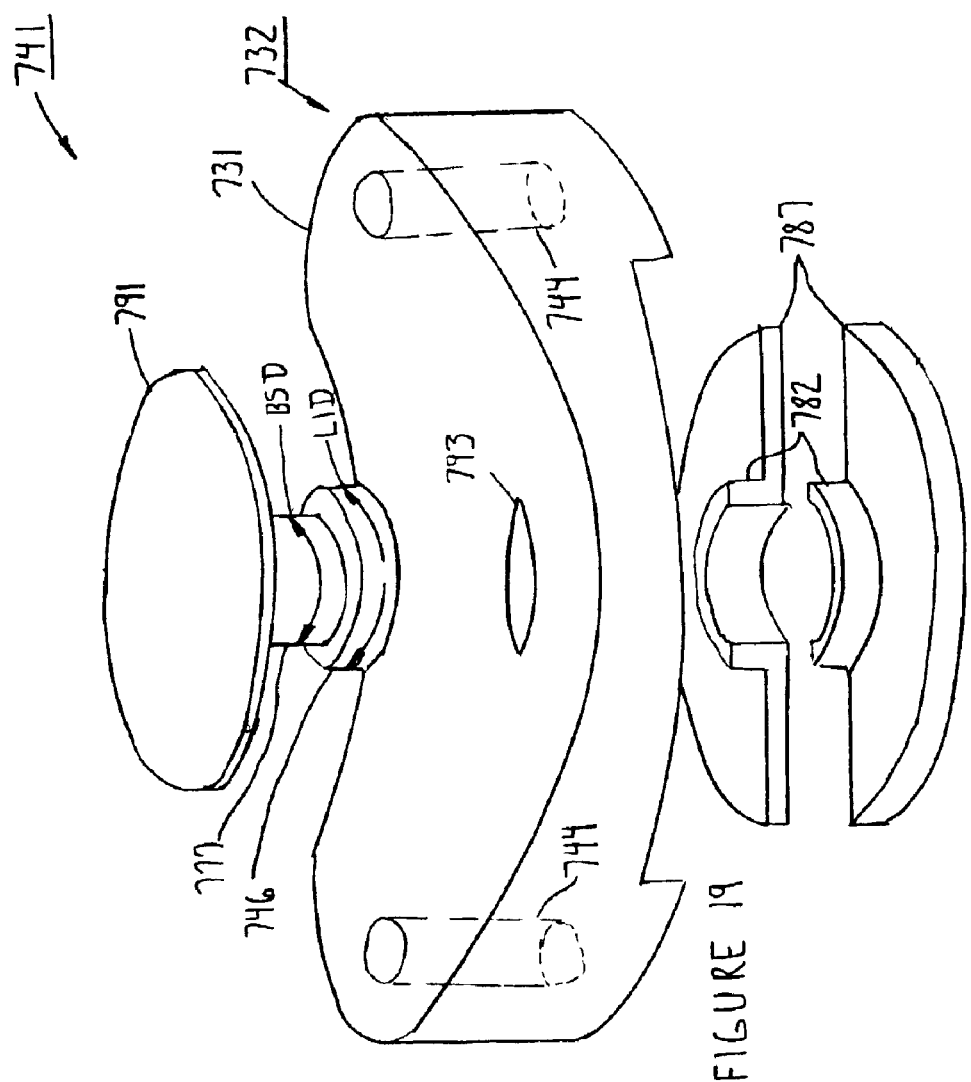
FIG. 19 is a partial exploded perspective view of the blade assembly of FIG. 18.
Figure 20:
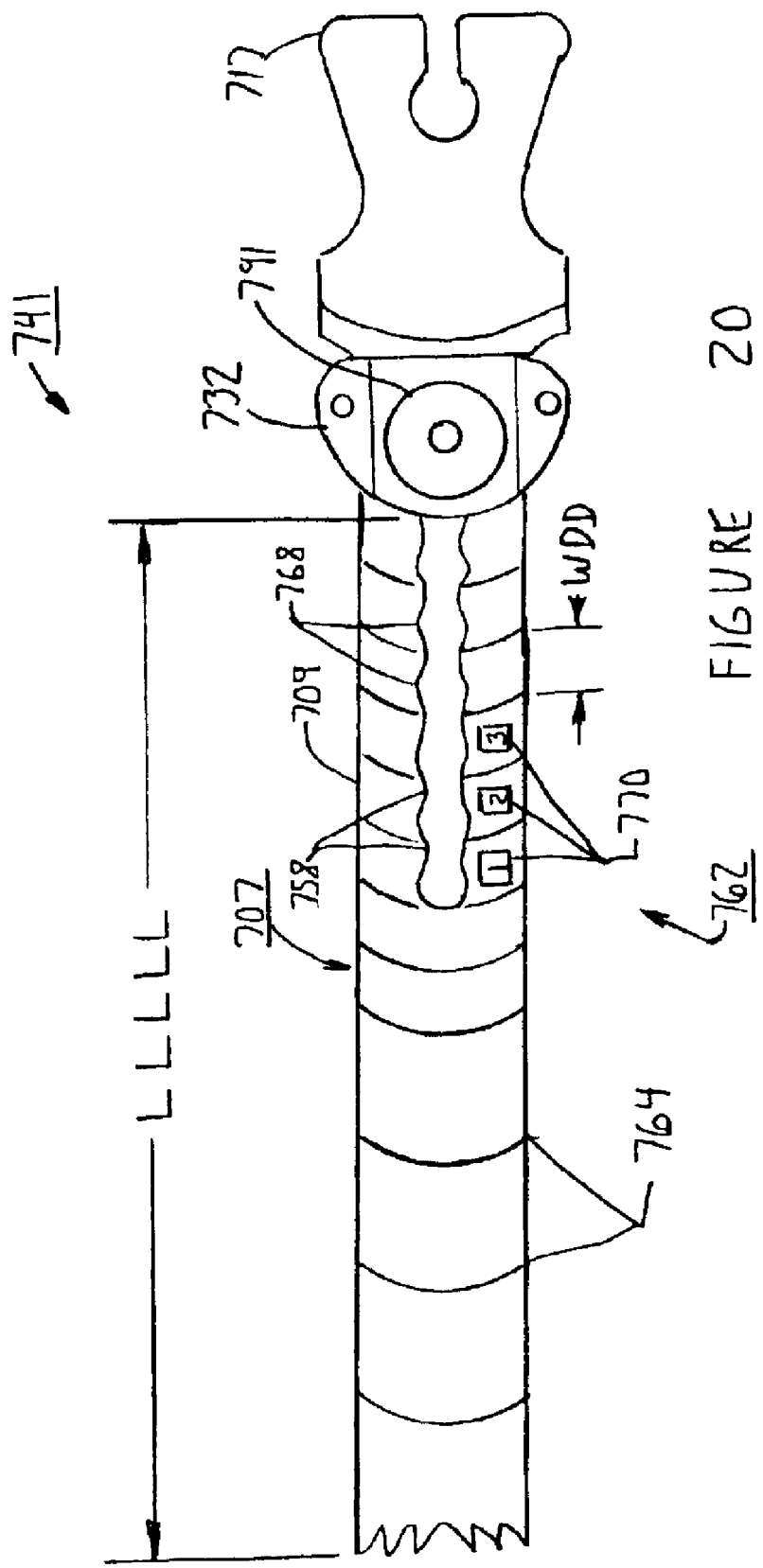
FIG. 20 is an plan view of the blade assembly of FIG. 18.

Referring now to FIGS. 18, 19, and 20, yet another embodiment of the present invention is shown as tool assembly 741. Tool assembly 741 includes a body 707 in the form of a blade. Blade 707 is similar to blade 107 of the tool assembly 141 of FIGS. 1 through 4. The tool assembly 741 further includes a cutting edge 730 extending along periphery 709 of the body 707. The cutting edge 730 is similar to cutting edge 30 of tool assembly 141 of FIGS. 1 through 4.

Tool assembly 741 further includes a stop 732. Stop 732 is substantially different from stop 32 of the tool assembly 141 of FIGS. 1 through 4. Referring again to FIGS. 18–20, the tool 726 further includes a positioning feature 750. The positioning feature 750 is substantially different from positioning feature 50 of the tool assembly 141 of FIGS. 1 through 4.

Positioning features 750 is in a form of an indented slot. The slot 750 maybe, as shown in FIGS. 18 through 20, a long narrow slot. The slot 750 extends completely across thickness TTT of the blade 707 forming an opening through the blade. The slot 750 has wide portions 758 and narrow portions 768. Each wide portion 758 corresponds to a position in which the stop may be fixedly positioned.

The stop 732 as shown in FIGS. 18, 19 & 20 includes a bottom portion 760 and an opposed top portion 731. The top portion 731 includes a through hole 793 through which the lip 746 and the button stem 777 of the button 791 slidably fits. A pair of retaining plates 787 are used to retain the button 791 within the tool hole 793 of the top portion 731. The retaining plate 787 include hubs 782 which are positioned between the through hole 793 and the button stem 777 to hold the button 791 in place in the top portion 731. The top portion 731 further includes guiding rails 781 which cooperate with periphery 709 of the blade 707 to maintain the angular orientation of the stop 732. The spring 797 is positioned between the top portion 731 and the bottom portion 760 to urge the button 791 in the direction of arrow 748. When the button 791 is in its upper position in the direction of arrow 748, the lip 746 is in position within the slot 750.

The lip 746 has a lip diameter LID which is generally the same as the lip WPW of the width portion 758 of the slot 750 such that when the button 791 is upward in the direction of arrow 748, the stop 732 is locked into one of the predetermined positions of the stop 732 along the blade 707.

The button stem 777, when the button 791 is manually depressed in the direction of arrow 743, is aligned with the narrow portions 768 of the slot 750. The button stem 777 has a button stem diameter via BSD which is smaller than the width of the slot 750 at the narrow portion 768 or smaller than narrow portion width NPW. Thus, when the button is depressed in the direction of arrow 743, the stop 732 may be moved along the direction of arrows 745 with the guiding rails 781 riding along the periphery 709 of the blade 707.

Screws 783 are slidably fitted through clearance holes 742 in the bottom portion 760 of the stop 732 and the screws 783 are threadably secured to the threaded holes 744 in the top portion 731 of the stop 732 to secure the top portion 731 to the bottom portion 760 of the stop 732. Top portion 798 of the spring 797 rests against the bottom face 785 of the button 791 urging the button in the direction of arrow 748.

By proper positioning of the stop 732 along the body or blade 707, the distance LLLLL between the cutting edge 730 and the face 766 may be adjusted such that when the tool assembly 741 is placed in the cutting block 16 (see FIG. 5) the cutting in 730 may be properly limited in its position.

The tool assembly 741 may further include indicia 762 on the blade 707. The indicia 762 may be in the form of lines 764 or numbers 770. The lines 764 may be separated from each other a distance of WDD of, for example, ten millimeters.

The tool assembly 741 may be connected to an oscillating saw (not shown) by any suitable method. For example, by hub 717 similar to hub 117 of the tool assembly 141 of FIGS. 1 through 4.

The blade 707 may be made of any suitable, durable material and may, for example, be made of a material which is similar to blade 107 of the tool assembly 141 of FIGS. 1 through 4. The stop 732 may be made of any suitable durable material capable of sterilization. For example, the bottom portion 760 and the-top portion 731 of the stop 732 may be made of a plastic, for example, polyethylene. The spring 797 may be made of a material similar to the spring 597 of the tool assembly 541 of FIGS. 14 and 15.

Figure 21:
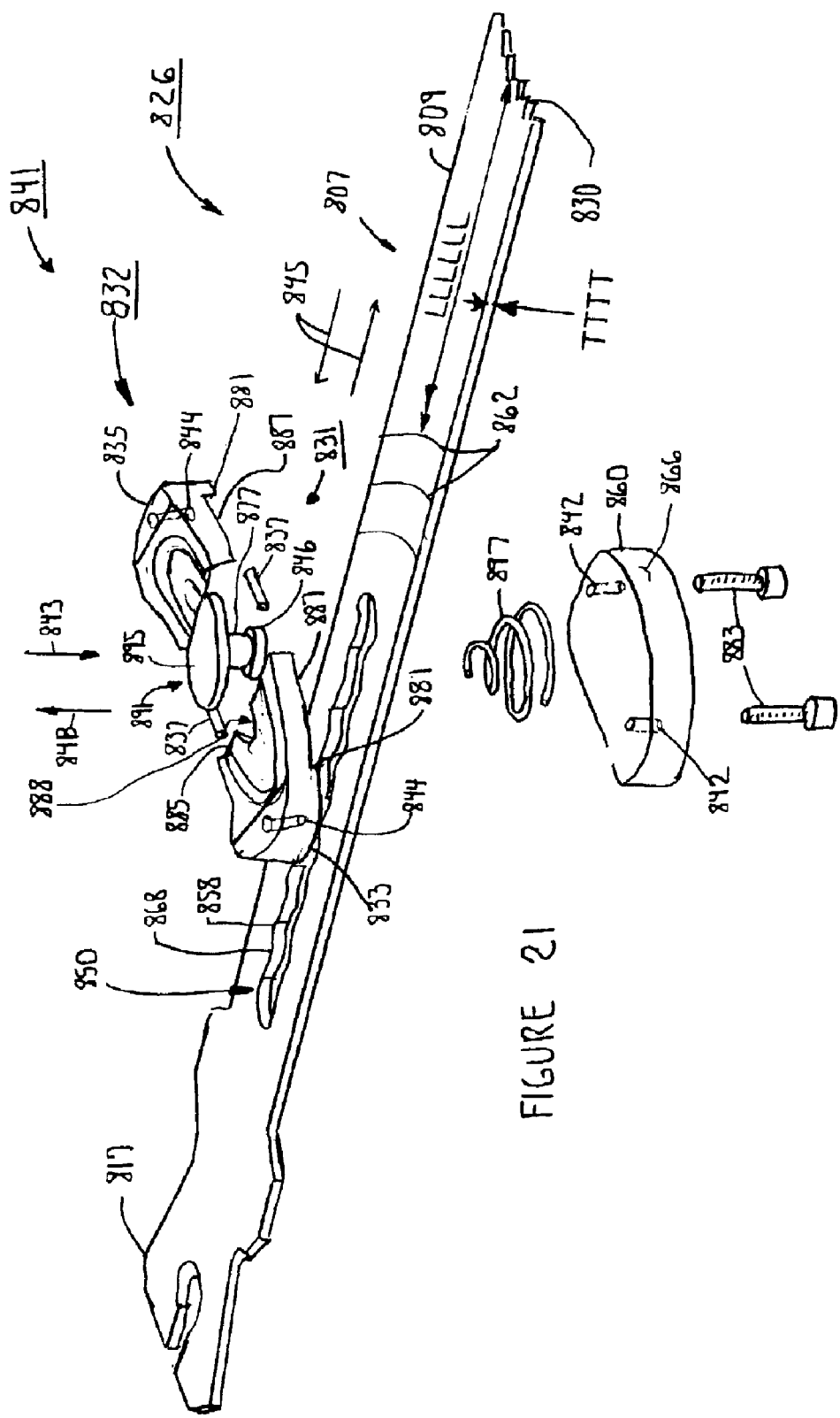
FIG. 21 is an exploded perspective view of a blade assembly including an adjustable stop for resecting bone for preparation of a total joint prosthesis implantation in accordance with yet another embodiment of the present invention.

Referring now to FIG. 21, another embodiment of the present invention is shown as tool assembly 841. Tool assembly 841 includes body 807 in the form of a blade. Blade 807 is similar to blade 107 of the tool assembly 141 of FIGS. 1 through 4. The tool assembly 841 further includes a cutting edge 830 extending along a periphery 809 of the body 807. The cutting edge 830 is similar to cutting edge 30 of the tool assembly 141 of FIGS. 1 through 4.

Tool assembly 841 further includes a stop 832. Stop 832 is substantially different from stop 32 of the tool assembly 141 of FIGS. 1 through 4. In fact stop 832 is more similar to the stop 732 of FIGS. 18 through 20.

Referring again to FIG. 21, the tool 826 further includes a positioning feature 850. The positioning feature 850 is substantially different from positioning 50 of the tool assembly 141 of FIGS. 1 through 4. Positioning feature 850 is in the form of an indented slot and is similar to positioning feature 750 of FIGS. 18–20. The slot 850, as shown in FIG. 21, is a long narrow slot and extends completely across thickness TTTT of the blade 807 forming an opening there through. The slot 850 has wide portions 858 and narrow portions 868. Each wide portion corresponds to a position where the stop may be fixedly positioned.

The stop 832, as shown in FIG. 21, includes a bottom portion 860 and an opposed top portion 831. The top portion 831 includes a first top portion half 833 and a second top portion 835. The top portions 833 and 835 are interconnected by, for example, pins 837.

A button 891 is positioned between the first top portion 833 and the second top portion 835. The top portions 833 and 835 include a retaining plate 887 which has a central opening 888. The button 891 includes a button stem 877 which slidably fits within the opening 888 of the retaining plate 887 of the top portions 833 and 835. The button 891 is trapped in the top portion 831 with the button stem 877 fitted with the opening 888 and the top face 895 of the button 891 and button lip 846 of the button 891 retaining the button 891 in position in the top portion 831.

The bottom portion 860 is secured to the top portion 831 by a pair of screws 883 which slidably fit through clearance holes 842 in the bottom portion 860 and which threadably are secured to the top portion 831 by threaded holes 844 in the top portion 831. A spring 897 is positioned between the bottom portion 860 and the top portion 831 and urges the button 891 in the direction of arrow 848.

When the button 891 is urged upwardly in the direction of arrow 848, button lip 846 is in position with wide portions 858 of the slot 850 fixedly positioning the stop 832 with respect to the blade 807. Guiding flats 881 in the top portion 831 are matedly fitted to periphery 809 of the blade 807 to guide the stop 832 in the direction of arrows 845.

When the button 891 is depressed in the direction of arrow 843, the button stem 877 is aligned with the slot 850 so that the stop 832 may freely slide in the direction of arrows 845 along the blade 807.

By proper position of the stop 832 along the body of blade 807, the distance LLLLL between the cutting edge 830 and the face 866 may be adjusted such that when the tool assembly 841 is placed in cutting blocks 16 (see FIG. 5) the cutting edge 830 may be properly limited in its position.

The tool assembly 841 may further include indicia 862 which may be in the form of lines or numbers. The lines may be separated from each other a distance of, for example, ten millimeters.

The tool assembly 841 may be connected to an oscillating saw (not shown) by any suitable method, for example, by hub 817 similar to hub 117 of the tool assembly 141 of FIGS. 1 through 4.

The blade 807 may be made of any suitable, durable material and made for example, be made of a material similar to blade 107 of the tool assembly 141 of FIGS. 1 through 4. The stop 832 may be made of any suitable, durable material capable of sterilization. For example, the bottom portion 860 and the top portion 831 of the stop 832 may be made of a plastic, for example polyethylene. The spring 897 may be made of a material similar to spring 597 of the tool assembly 541 of FIGS. 14 and 15.

Although the present invention and its advantages have been described in detail, it should be understood that various changes, substitutions, and alterations can be made therein without departing from the spirit and scope of the present invention as defined by the appended claims.

What is claimed is:

1. A tool for resection of bone for use in preparation of a cavity for implantation of a joint prosthesis, said tool being cooperable with a tool stop and fittable within an opening of a tool guide in cooperation with the bone, said tool comprising:
   a body defining a periphery thereof, a portion of said body being constrainable within the opening of the guide;
   a cutting edge adapted for resection of bone and positioned along a portion of the periphery of said body; and
   a plurality of position features associated with said body, said position features being cooperable with the guide and the stop for limiting the movement of said tool within the guide so that the position of said cutting edge with respect to the bone may be controlled.

2. The tool of claim 1, wherein said body comprises a blade.

3. The tool of claim 1, wherein said body is adapted to permit the stop to be slidably positionable along said body.

4. The tool of claim 1, wherein said body is adapted to permit the stop to surround at least a portion of said body.

5. The tool of claim 1, wherein each of said plurality of position features is spaced along the length of said tool.

6. The tool of claim 1, wherein apertures formed in said body define said position features.

7. The tool of claim 1, wherein at least one of said position features and the stop are biased into engaging position with each other.

8. The tool of claim 1, wherein said body has indicia thereon corresponding to at least one of said plurality of position features.

9. A tool assembly for resection of bone for use in preparation of a cavity for implantation of a joint prosthesis, a portion of said tool assembly being fittable within an opening of a tool guide in cooperation with the bone, said tool assembly comprising:

a body defining a first end thereof;

a cutting edge extending from a first end of said body, said edge adapted for resection of bone; and a stop cooperable with said body and the guide for limiting the movement of said body within the guide so that the position of said cutting edge with respect to the bone may be controlled, said stop adapted for having a plurality of stop positions with respect to at least one of said body and the guide, said body being constrainable within the opening of the guide, and said body being cooperable with the guide and said stop for limiting the movement of said body within the guide so that the position of said cutting edge with respect to the bone may be controlled, said body having a plurality of position features for assisting in positioning said stop in one of the stop positions.

10. The tool assembly of claim 9, wherein said body comprises a blade.

11. The tool assembly of claim 9, wherein at least one of said body and said stop are adapted to permit said stop to be slidably positionable along said body.

12. The tool assembly of claim 9, wherein said body is adapted to permit said stop to surround at least a portion of said body.

13. The tool assembly of claim 9:

wherein said stop includes a stop feature; and wherein said body includes a plurality of body features, each of said plurality of body features adapted to cooperate with said stop and each of said plurality of body features corresponding to one of said plurality of stop positions along said body.

14. The tool assembly of claim 9:

wherein said stop defines a stop aperture;

wherein said body defines a plurality of tool apertures, each of said stop positions corresponding to one of the tool apertures; and further comprising a pin to interconnect said stop to said body at one of the tool apertures and at the stop aperture said body having a plurality of position features.

15. The tool assembly of claim 9, wherein said tool features are biased into engaging position with said stop.

16. The tool assembly of claim 9, wherein said body has indicia thereon corresponding to said plurality of positions.

* * * * *